United States Patent
Felicetti et al.

(10) Patent No.: US 7,645,759 B2
(45) Date of Patent: Jan. 12, 2010

(54) NON-PEPTIDE BRADYKININ ANTAGONISTS AND PHARMACEUTICAL COMPOSITIONS THEREFROM

(75) Inventors: Patrizia Felicetti, Rome (IT); Christopher Ingo Fincham, Pomezia (IT); Alessandro Giolitti, Florence (IT); Carlo Alberto Maggi, Florence (IT); Laura Quartara, Florence (IT); Cristina Rossi, Pomezia (IT)

(73) Assignee: Istituto Luso Farmaco D'Italia S.p.A. (IT)

( * ) Notice: Subject to any disclaimer, the term of this patent is extended or adjusted under 35 U.S.C. 154(b) by 0 days.

(21) Appl. No.: 11/786,041

(22) Filed: Apr. 10, 2007

(65) Prior Publication Data

US 2007/0281944 A1 Dec. 6, 2007

Related U.S. Application Data

(63) Continuation of application No. PCT/EP2005/010412, filed on Sep. 27, 2005.

(30) Foreign Application Priority Data

Oct. 15, 2004 (IT) .............................. MI04A1963

(51) Int. Cl.
A61K 31/4709 (2006.01)
C07D 405/12 (2006.01)
A61K 31/47 (2006.01)
C07D 215/26 (2006.01)

(52) U.S. Cl. .................................. 514/253.06; 544/363
(58) Field of Classification Search .................... None
See application file for complete search history.

(56) References Cited

FOREIGN PATENT DOCUMENTS

| WO | 03/103671 A1 | * | 12/2003 |
| WO | 2006/040004 | * | 4/2006 |
| WO | 2007/003411 A2 | * | 1/2007 |

OTHER PUBLICATIONS

Tramontana et al. Journal of Pharmacology and Experimental Therapeutics, vol. 296, pp. 1051-1057, 2001.*
Bock et al. Current Opinion in Chemical Biology, vol. 4, p. 401-406 (2000).*
Howl et al. Expert Opin.Ther. Targets, vol. 7(2) (2003).*
Valenti et al. Journal of Pharmacology and Experimental Therapeutics,vol. 315, p. 616-623 (first published on the web on Jul. 18, 2005).*
Fattori et al. Jounal of Medicinal Chemistry, vol. 50, p. 550-565 (first published on the web on Jan. 6, 2007).*

* cited by examiner

Primary Examiner—Emily Bernhardt
(74) Attorney, Agent, or Firm—Lerner, David, Littenberg, Krumholz & Mentlik, LLP

(57) ABSTRACT

Non-peptide compounds having activity as selective antagonists of bradykinin (BK) B2 receptor are disclosed. The compounds have the general formula (I)

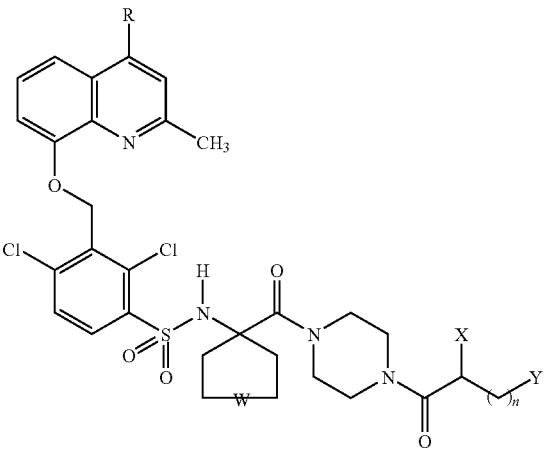

in which R is hydrogen or methyl; W is a single bond or an oxygen atom; n=3; X is hydrogen or a —$NR_1R_2$ amino group in which $R_1$ and $R_2$ can be independently hydrogen or a group which is methyl, ethyl, n-propyl, or isopropyl; Y is a —$NR_3R_4R_5$ quaternary ammonium group in which $R_3$, $R_4$, $R_5$ can be independently a group which is methyl, ethyl, n-propyl, isopropyl, n-butyl, isobutyl, or n-pentyl; and the enantiomers and enantiomeric mixtures thereof. Pharmaceutical compositions containing these compounds and methods of using the compounds to treat patients having conditions, disorders or diseases involving activation of bradykinin B2 receptors are also disclosed.

13 Claims, No Drawings

NON-PEPTIDE BRADYKININ ANTAGONISTS AND PHARMACEUTICAL COMPOSITIONS THEREFROM

PRIORITY

The present application is a continuation of International Application No. PCT/EP2005/010412 filed Sep. 27, 2005, published in English, which claims priority from MI 2004 A001963 filed Oct. 15, 2004, all of which are incorporated herein by reference.

FIELD OF THE INVENTION

The present invention relates to non-peptide compounds containing a quaternary ammonium group, having activity as specific antagonists of bradykinin (BK) B2 receptor, pharmaceutical compositions containing them and the use thereof for the treatment of all the conditions in which activation of bradykinin B2 receptors are involved.

BACKGROUND OF THE INVENTION

Bradykinin (BK) belongs to kinins and forms, together with kallidin and T-kinin, the sub-group of kinins present in mammals. Kinins play an important role as mediators of pain and inflammation, both in the central and peripheral nervous system. Bradykinin is, in particular, a nonapeptide produced by the body in physiopathological conditions.

Two types of kinins receptors exist, B1 and B2. The main characteristic of the B1 receptor is that it is more inducible than constitutive. It is expressed in tissues in inflammation or stress conditions. On the other hand, B2 is a constitutive receptor normally present in all tissues and acts a mediator during the inflammatory processes. Bradykinin and kallidin are released from their protein precursors (known as kininogens), by proteolytic enzymes named kininogenases. Among these, the main role is played by kallikreins which however, once released by the precursor, can exert their action only for a short time as they are quickly destroyed by a series of circulating enzymes and membranes generically defined as kininases. One of these kininases cleaves bradykinin at the C-terminal arginine thus forming a des-Arg-BK which acts as B1 receptor agonist.

The activation of bradykinin B1 and B2 receptors induces relaxation of vasal muscles with consequent hypotension, increase in vascular permeability, contraction of smooth muscles of intestine and respiratory tract, stimulation of nociceptive neurons, alteration of ionic epithelial secretion, production of nitroxide and release of cytokines by leukocytes and eicosanoids from different cell types. As a consequence, antagonistic compounds of BK receptors can be considered a novel class of medicaments supposedly active in various disorders. Possible therapeutical applications for said antagonists are inflammatory, allergic and autoimmune disorders, such as asthma and chronic bronchitis (also induced by irritants), allergic, vasomotor and viral rhinitis, obstructive pulmonary disease (COPD), rheumatoid arthritis, chronic inflammatory diseases of the bowel (Crohn's disease and ulcerative colitis), glomerulonephritis, psoriasis, rash, acute and chronic cystitis; degenerative disorders characterized by fibrosis, such as hepatic cirrhosis, glomerulopathies and pulmonary fibrosis, arteriosclerosis; thanks to their analgesic activity, in the treatment of both acute and chronic pain, for example in burns, cephalea, insects bites, chronic pain in cancer patients; in disorders of the cardiovascular apparatus such as septic, allergic and post-traumatic shocks, and hepatic cirrhosis by hepatorenal syndrome; as anticancer and antiangiogenetics; in the treatment of hypotension and of alopecia.

Different peptide and non-peptide antagonists of bradykinin B2 receptor are known in literature. Intellectual Property Publication WO03103671 discloses a large family of compounds with antagonistic activity on bradykinin B2 receptor. The compounds of the present invention, although being included in the general formula of WO03103671, are not described or characterized in said document.

SUMMARY OF THE INVENTION

A first aspect of the present invention is directed to compounds of the general formula (I):

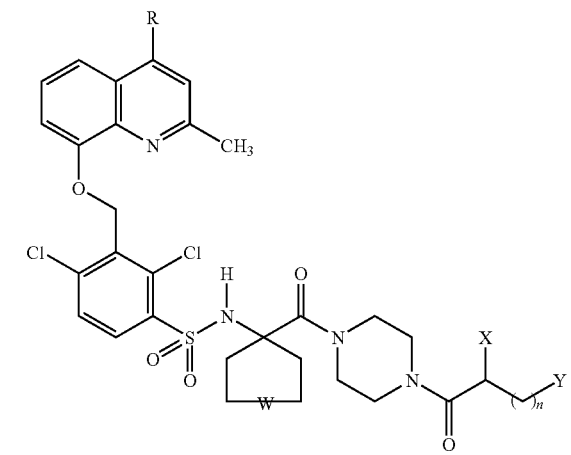

in which:
R is hydrogen or methyl;
W is a single bond or an oxygen atom;
n=3, or 4;
X is hydrogen or a —$NR_1R_2$ amino group in which $R_1$ and $R_2$ can be independently hydrogen or a group selected from methyl, ethyl, n-propyl and isopropyl;
Y is a —$NR_3R_4R_5$ quaternary ammonium group in which $R_3$, $R_4$, $R_5$ can be independently a group selected from methyl, ethyl, n-propyl, isopropyl, n-butyl, isobutyl and n-pentyl; and the salts thereof with pharmaceutically acceptable acids.

Another aspect of the present invention is directed to a pharmaceutical composition containing a compound of general formula (I), or a salt thereof with a pharmaceutically acceptable acid, and pharmaceutically acceptable excipients or carriers.

A third aspect of the present invention is directed to a method of treating a patient with a condition, disorder or disease involving activation of bradykinin B2 receptor, which entails administration to the patient of an effective dose of a compound of general formula (I).

DETAILED DESCRIPTION OF THE INVENTION

The present invention relates to non-peptide compounds which show high affinity and antagonistic activity towards B2 receptor, having general formula (I):

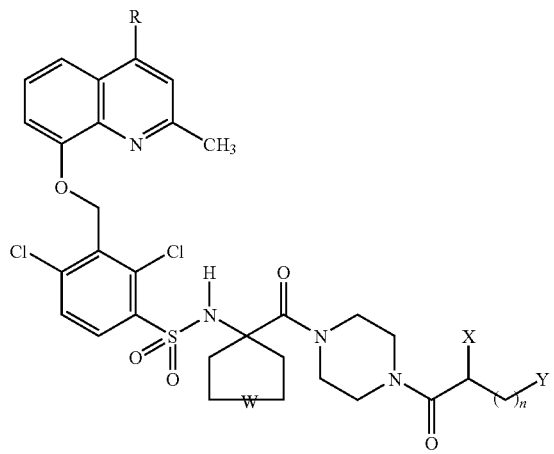

(I)

in which:
R is hydrogen or methyl;
W is a single bond or an oxygen atom;
n=3 or 4;
X is hydrogen or a —NR$_1$R$_2$ amino group in which R$_1$ and R$_2$ can be independently hydrogen or a group selected from methyl, ethyl, n-propyl and isopropyl;
Y is a —NR$_3$R$_4$R$_5$ quaternary ammonium group in which R$_3$, R$_4$, R$_5$ can be independently a group selected from methyl, ethyl, n-propyl, isopropyl, n-butyl, isobutyl and n-pentyl; and the salts thereof with pharmaceutically acceptable acids.

Preferably, compounds (I) are salified with inorganic or organic acids selected from hydrochloric, hydrobromic, hydroiodic, sulfuric, phosphoric, acetic, trifluoroacetic, propionic, oxalic, malic, maleic, succinic, malonic, aspartic and glutamic acids. Moreover, due to the presence of a chiral center, the invention also comprises the two enantiomers or mixtures thereof, in any proportion, including racemic mixtures.

The compounds of general formula (I) have both in vivo and in vitro antagonistic activity towards B2 receptor higher than the more structurally similar analogues as described in WO03103671.

Preferred are the compounds of general formula (I) in which:
n=3;
X=hydrogen or a —NH$_2$ group;
Y=—N(CH$_3$)$_3$$^+$ quaternary ammonium group;
the other substituents being as defined above.

Particularly preferred are the compounds (I) wherein:
R is hydrogen or methyl;
W is an oxygen atom;
n=3;
X is hydrogen or a group —NH$_2$; and
Y is a —N(CH$_3$)$_3$$^+$ quaternary ammonium group.

The compounds of the present invention can be prepared according to well known synthetic routes.

Preferably, the compounds of general formula (I) as defined above are prepared by condensation, in the presence of a suitable condensing agent, of the intermediate of general formula (II), obtained as disclosed in WO03103671

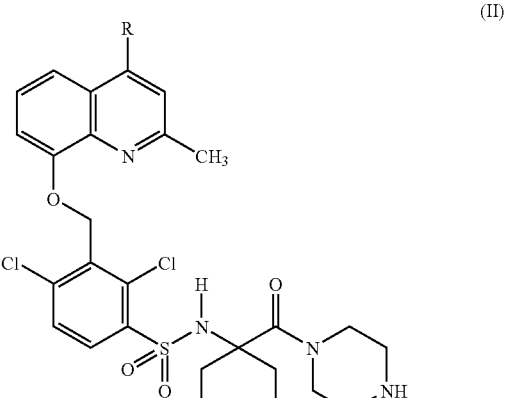

(II)

with the compound of formula (10)

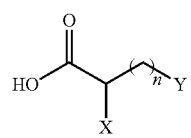

(10)

or a derivative thereof in which the carboxylic group is suitably activated.

The synthetic process is illustrated in Scheme 1

Scheme 1

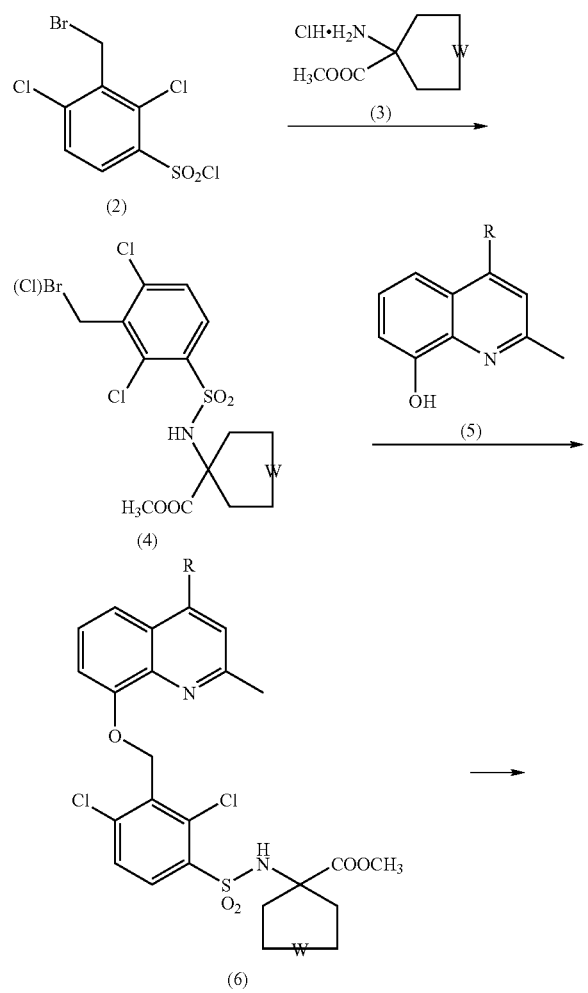

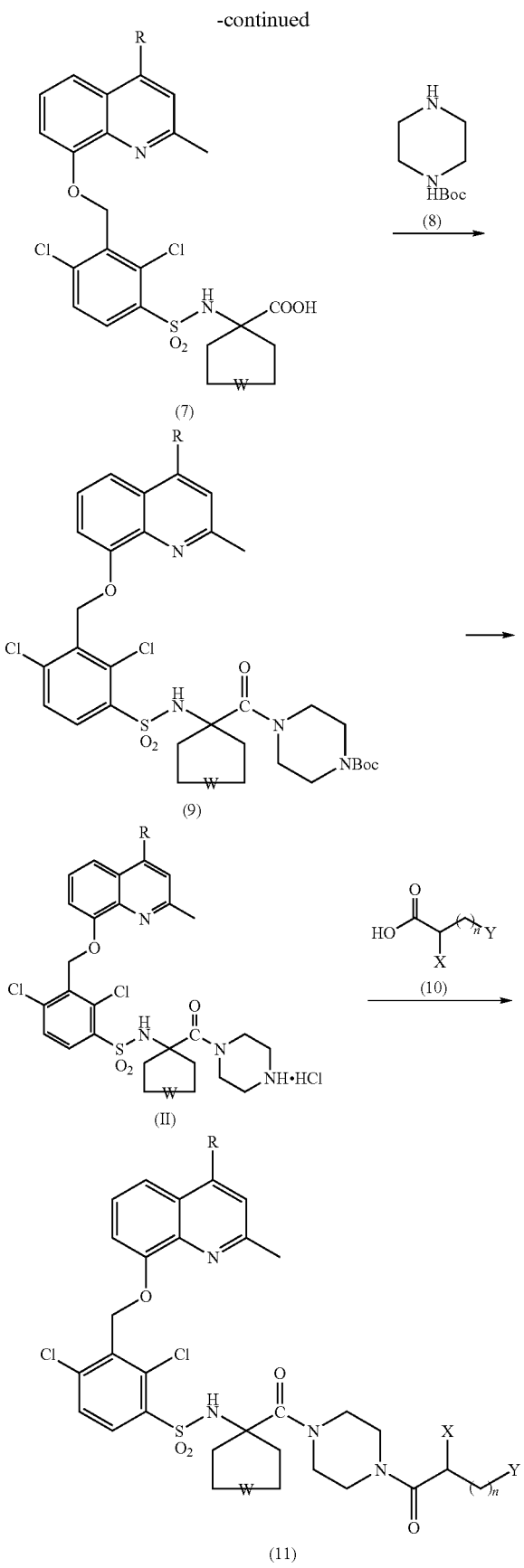

The compound of formula (2) is prepared as described in Blaney, et al., J. Med. Chem. 44:1675-1689 (2001), by bromination of the corresponding toluene derivative, which is in turn obtained as described in Kageyama, et al., J. Fluorine Chemistry 101:85-89 (2000).

The first step concerns the formation of the sulfonamido bond (4) obtained by condensation of intermediates (2) and (3). This reaction is carried out at room temperature, preferably in acetonitrile/water (2:1), in the presence of sodium hydrogen carbonate ($NaHCO_3$). Said reaction takes place with exchange of chlorine and bromine at the benzyl position: the resulting products mixture is directly used in the subsequent step. The reaction of the halogen derivatives mixture with a disubstituted hydroxyquinoline (5), in the presence of potassium carbonate ($K_2CO_3$) and potassium iodide (KI), in acetone under reflux, yields the ester derivative (6).

The compound of formula (5) i.e. 2,4-dimethyl-8-hydroxy quinoline, in which $R4=R5=CH_3$, is prepared as disclosed in WO9640639.

The methyl ester of formula (6) is hydrolysed under basic conditions to carboxylic acid (7), which is condensed with Boc-piperazine (8), to yield intermediate (9). The condensation reaction is carried out according to a known procedure for the peptide synthesis, using hydroxybenzotriazole to activate the carboxylic moiety, a condensing agent such as 1-ethyl-3-(3'-dimethylpropyl) carbodiimide and an amount of tertiary amine, namely diisopropylethylamine, of three equivalents on the basis of the condensing agent. Compound (II) is obtained by cleavage of the Boc group from intermediate (9), by means of a hydrochloric acid solution (4N) in dioxane and isolating the free amine instead of the hydrochloride.

Derivative (11) is obtained by condensation of intermediate (10) with the amino acid (11) according the procedure described for the preparation of (9) from (7). Any Boc group present can be removed from intermediate (11), with a hydrochloric acid solution (4N) in dioxane, thus obtaining the final compound. When case the trialkylammonium group is not present in any commercially available intermediates, it can be synthesized starting from the corresponding amine with known procedures (Rapoport et al., J. Org. Chem. 42:139-141 (1977); Chen, et al., Canadian J. Biochem. 56:150-152 (1978)).

The compounds of the invention are used in the treatment of all those disorders in which the activation of bradykinin receptor has to be blocked or reduced. They are particularly suitable for the treatment of inflammatory, allergic and autoimmune disorders, such as asthma and chronic bronchitis, allergic, vasomotor and viral rhinitis, chronic obstructive pulmonary disease (COPD), rheumatoid arthritis, chronic inflammatory diseases of the bowel (Crohn's disease and ulcerative colitis), glomerulonephritis, psoriasis, rash, acute and chronic cystitis, hepatic cirrhosis, glomerulopathies and pulmonary fibrosis, arteriosclerosis, both acute and chronic pain, septic, allergic and post-traumatic shocks, hepatic cirrhosis by hepatorenal syndrome, hypotension, alopecia, or as anticancer or antiangiogenetic agents.

For use in therapy, the compounds of the invention will be suitably formulated together with pharmaceutically acceptable carriers/excipients. Preferred are pharmaceutical forms suitable for the oral administration, such as tablets, capsules, granules, powders, solutions, suspensions, syrups or the like. These pharmaceutical preparations can be prepared with conventional procedures using ingredients known in technique, such as ligands, disintegrants, lubricants, fillers, stabilizing agents, diluents, dyes, flavours, wetting agents and other excipients known to those skilled in the art. The oral formulations also comprise protracted-release forms, such as enteric-coated tablets or granules. The solid oral compositions can be prepared with conventional mixing, filling or compression methods. The liquid oral preparations can be in the form of, for example, aqueous or oily suspensions or solutions, emulsions, syrups, or can be presented as dry product for reconstitution with water or other suitable carrier before use.

The dosage can range depending on the age and general conditions of the patient, nature and severity of the disease or disorder and route and type of administration. As a rule, in case of oral administration to a human adult patient, the compounds of the present invention will be generally administered in a total daily dosage ranging from 1 to 1000 mg, preferably from 5 to 300 mg, in a single dose or in subdivided doses.

The following examples illustrate the invention in greater detail.

EXAMPLE 1

(4-(S)-amino-5-(4-{4-[2,4-dichloro-3-(2,4-dimethyl-quinolin-8-yloxymethyl)-benzenesulfonylamino]tetrahydropyran-4-carbonyl}piperazin-1-yl)-5-oxo-pentyl]trimethyl-ammonium chloride, dihydrochloride (Compound of general formula I in which R=$CH_3$, W=—O—, X=$NH_2$, n=3, Y=$N(CH_3)_3{}^+C^-$).

The compound was synthesized following the synthetic route illustrated in Scheme 2.

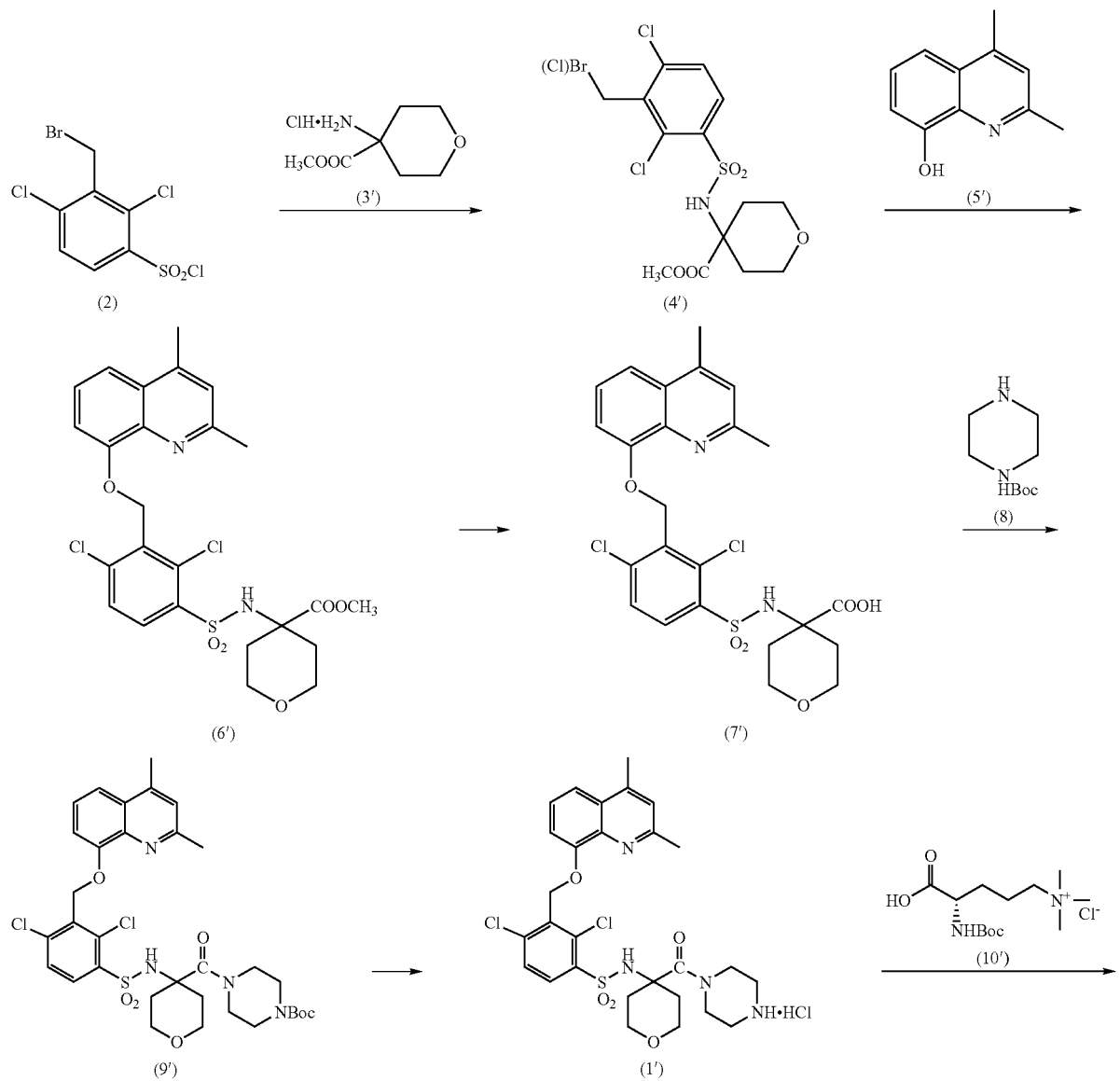

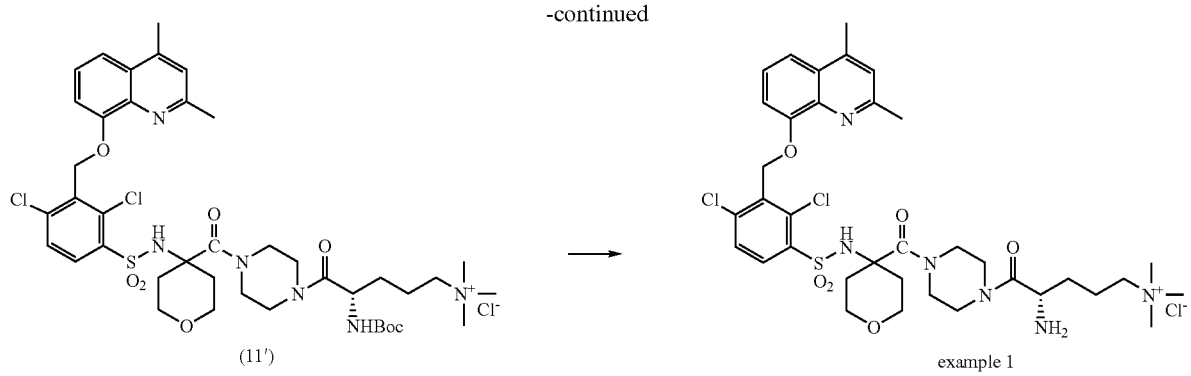

(11')  →  example 1

GENERAL METHODS: analytic HPLC: Flow: 1 ml/min; Mobile phase: A-0.1% trifluoroacetic acid in water, B-0.1% trifluoroacetic acid in acetonitrile; Column: Zorbax Eclipse XDB C8, 5 micron, 150×4,6 mm.

Intermediate (2) 2,4-Dichloro-3-bromomethyl-benzenesulfonyl chloride 10 ml of chlorosulfonic acid were dropwise added with 4.8 ml of 2,6-dichlorotoluene in two hours, under magnetic stirring at room temperature. After completion of the addition, the mixture was heated at 40° C. for two hours, thereby obtaining a purple solution, which was cooled and carefully poured into ice-water (0.5 l), stirring vigorously. The separated white solid was filtered, triturated, washed with water, dried over KOH and purified by washing with n-hexane, adding 200 ml of solvent under strong stirring. The mixture was filtered, the solid was discarded and the solvent was evaporated to dryness to obtain 2,4-dichloro-3-methyl-benzenesulfonyl chloride as a crystalline white solid. Yield: 85%.

HPLC purity: 86% (30% B, 3%/min, Rt=19.7 min).

1H-NMR (CDCl3): δ (ppm) 2.6 (s, 3H), 7.5 (d, 1H), 7.95 (d, 1H); ESI(+)MS: m/z 260 [M+H]+.

This intermediate was brominated under the following conditions:

20 mmols of 2,4-dichloro-3-methyl-benzenesulfonyl chloride were dissolved in acetonitrile. 2 eq of NBS were added under stirring at room temperature until completed solubilization of NBS. Finally, 0.1 eq of azo-bisisobutyronitrile (AIBN) was added and the mixture was heated at 70° C. for approx. 6 hours. The solution was evaporated, the residue was taken up with ethyl acetate, washed with H$_2$O and 5% NaHCO$_3$, dried over dry Na$_2$SO$_4$ and filtered. The organic phase was evaporated thereby obtaining a viscous, light colored liquid which was taken up into petroleum ether. The residue was filtered, and the solution yielded (2') as a light colored crystalline solid.

HPLC purity: 95% (50% B to 5%/min, Rt=18.72).

1H-NMR (CDCl3): δ (ppm) 4.85 (s, 2H), 7.58 (d, 1H), 8.08 (d, 1H); ESI(+)MS: m/z 338.1 [M+H]+.

Intermediate (3') 4-Amino-tetrahydropyran-4-carboxylic acid methyl ester hydrochloride 4-Amino-tetrahydropyran-4-carboxylic acid hydrochloride (0.025 mols) was suspended in 13 ml of CH$_3$OH, cooled to −60° C. and dropwise added with SOCl$_2$ (3 eq) under stirring. After completion of the addition, the mixture was left to warm to room temperature, then gradually heated to ebullition to obtain a clear solution (approx. 2 hours), which was cooled, the residue was filtered and concentrated under vacuum.

Yield 80%. Purity (NMR): 85%.

1H-NMR (DMSO-d6): δ (ppm) 1.91-2.04 (m, 4H), 3.78 (s, 3H), 3.60-3.85 (m, 4H), 9.00 (s, 3H). ESI(+)MS: m/z 160.1 [M+H]+.

Intermediate (4') 4-(3-Bromomethyl-2,4-dichloro-benzenesulfonylamino)-tetrahydropyran-4-carboxylic acid methyl ester The intermediate (3') (1.1 eq) was dissolved in water together with 4 equivalents of K$_2$CO$_3$. This solution was added with a solution of 1 equivalent (10 mmols) of intermediate (2) in acetonitrile and stirred at room temperature until a precipitate formed (4 hours). The solvent was evaporated off and the residue was dissolved in ethyl acetate and 0.1M HCl (1/1). The organic phase was separated and dried over Na$_2$SO$_4$. The solvent was evaporated off, and the resulting solid was washed with cyclohexane, thereby obtaining a white solid in which chloro/bromo derivatives were present in 10/1 ratio. Yield: 60%.

HPLC purity: 88% (20% B at 3%/min; Rt=14.11 (Br) and 14.47 (Cl)).

1H-NMR (CDCl3): δ (ppm) 1.81-1.99 (2H, m), 2.07-2.25 (2H, m), 3.49-3.71 (7H, m), 4.81 (1.5H, s, [Br]), 4.94 (0.3H, s, [Cl]), 5.30 (1H, brs), 7.47-7.53 (1H, m), [7.49 (d, J 8.5Hz, X=Br), 7.51 (d, J 8.5Hz, X=Cl], 7.91-7.98 (1H, m), [7.94 (d, J 8.5Hz, X=Br), 7.96 (d, J 8.5Hz, X=Cl].

Intermediate (6') 4-[2,4-Dichloro-3-(2,4-dimethyl-quinolin-8-yloxymethyl)-benzenesulfonylamino]tetrahydropyran-4-carboxylic acid methyl ester Quinoline (5') (0.48 mmols) and LiOH (2.5 eq) were mixed at room temperature under nitrogen in methyl ethyl ketone (MEK). The mixture was kept under stirring and under nitrogen for 90 min. Intermediate (4) was dissolved in MEK/dry DMF (2/1) (42 ml, 12 ml/mmol), and the solution containing the quinoline was dropwise added to the reaction mixture, under stirring. Stirring was kept for 16 hours. The reaction mixture was concentrated under vacuum and the residue dissolved in ethyl acetate (50 ml, 100 ml/mmol). The organic phase was washed (3×50 ml) with a buffer solution Ph=4.2, dried over Na$_2$SO$_4$, filtered and concentrated under vacuum to obtain a yellow oil. Yield: 33%. HPLC purity: 77% (20% B, 3%/min; Rt=9.54).

1H-NMR (DMSO-d6): δ (ppm) 1.80-1.95 (m, 4H), 2.56 (s, 3H), 2.64 (s, 3H), 3.32-3.40 (m, 2H), 3.42-3.55 (m, 2H), 3.60 (s, 3H), 5.57 (s, 2H), 7.30 (s, 1H), 7.39 (d, 1H), 7.50 (dd, 1H), 7.67 (d, 1H), 7.78 (d, 1H), 8.02 (d, 1H), 8.77 (bs, 1H); ESI (+)MS: m/z 553.1 [M+H]+.

Intermediate (7') 4-[2,4-Dichloro-3-(2,4-dimethyl-quinolin-8-yloxymethyl)-benzenesulfonylamino]tetrahydropyran-4-carboxylic acid Intermediate of formula (6') was dissolved in THF and the solution was added with 10 eq of 1M LiOH in water. The mixture was stirred for 4 hours at 40° C., then the solvent was evaporated off. The residue was dissolved in water and 0.1M HCl was added to pH=4. The aqueous phase was extracted with dichloromethane and the organic phase was dried over $Na_2SO_4$. Solvent was evaporated off to obtain a yellow solid residue. Yield: 90%. HPLC purity: 99% (20% B, 3%/min; Rt=7.72).

1H-NMR (DMSO-d6): δ (ppm) 1.75-1.90 (m, 4H), 2.56 (s, 3H), 2.64 (s, 3H), 3.10-3.35 (m, 2H), 3.38-3.50 (m, 2H), 5.58 (s, 2H), 7.30 (s, 1H), 7.37 (d, 1H), 7.46 (t, 1H), 7.67 (d, 1H), 7.75 (d, 1H), 8.03 (d, 1H), 8.64 (bs, 1H). ESI(+)MS: m/z 539.1 [M+H]+.

Intermediate (9') 4-tert-butoxycarbonyl-((4-(2,4-dichloro-3-(2,4-dimethyl-quinolin-8-yloxymethyl) benzenesulfonylamino)-tetrahydropyran-4-carbonyl)-piperazin-1-yl)

(7') (1.3 mmols) and HOBt (1.1 eq) were suspended in 50 ml of dry DMF in a 100 ml round-bottom flask under nitrogen. The mixture was cooled to +4° C. and added with EDCI.HCl (1.1 eq) under stirring. Stirring at +4° C. was continued for an hour, then DIPEA (2 eq) and Boc-piperazine (1 eq) were added and the mixture was left to warm to room temperature, under stirring. After 12 h the solvent was evaporated off, the residue was dissolved in 40 ml of DCM and the organic phase was washed with brine (20 ml) and dried over $Na_2SO_4$. The solvent was evaporated off to obtain an oil which was purified on a Varian Mega Bond (flash master system) 70 g column (ethyl acetate, Rf=0.50), thereby obtaining a yellow solid.

Yield: 96%. HPLC purity: 98% (20% B, 3% B/min, Rt=11.14).

1H-NMR (CDCl3): δ (ppm) 1.45 (s, 9H); 1.55-1.80 (m, 2H), 2.05-2.20

(m, 4H), 2.56 (s, 3H), 2.64 (s, 3H), 3.38-3.90 (m, 10H), 5.58 (s, 2H), 7.10 (s, 1H), 7.30 (s, 1H), 7.37 (d, 1H), 7.46 (t, 1H), 7.67 (d, 1H), 7.75 (d, 1H), 8.03 (d, 1H), 8.64 (bs, 1H). ESI(+)MS: m/z 707.2 [M+H]+.

Intermediate (1') (4-(2,4-Dichloro-3-(2,4-dimethyl-quinolin-8-yloxymethyl)-benzenesulfonylamino)-tetrahydropyran-4-carbonyl)-piperazin-1-yl 0.62 mmols of (9') were added with 10 ml of HCl/dioxane 4M and the mixture was kept under stirring for 3 hours. The solvent was evaporated off and the residue was freeze-dried, to obtain hydrochloride (1') as yellow solid. Yield: 98%. HPLC purity: 92% (20% B, 3%/min; Rt=5.34).

1H-NMR (D2O): δ (ppm) 1.55-2.10 (m, 7H), 2.90-3.10 (m, 9H), 3.20-3.55 (m, 9H), 6.0 (s, 2H), 7.60-8.10 (m, 8H), 8.95 (d, 1H).

ESI(+)MS: m/z 609.1 [M+H]+.

Intermediate (10') (4-tert-butoxycarbonylamino-4-carboxy-butyl)-trimethylammonium 10 mmols of Boc-Orn-OH were suspended in methanol (20 ml) and the suspension was added with 44 mmols of isourea. The flask was plugged and kept under stirring at room temperature for 2 days. The resulting solution was monitored by TLC (eluent: $CHCl_3/CH_3OH/NH_4OH$ 40/54/6; Boc-Orn-OH Rf=0.29; (10') Rf: 0.11, detection $KMnO_4$).

Methanol was evaporated off under vacuum and the residue was digested in 150 ml of water and filtered. The round-bottom flask and the solid were washed with water (2×50 ml) and all the washing aqueous fractions were combined, then concentrated under vacuum (40 ml). The resulting solid (4.068 g) was suspended in water (40 ml), filtered (to remove any traces of urea) and purified by FCC on reversed phase LiChroprep RP-18 (40-63 micron). The column (19×7 cm) was eluted with 3% $CH_3CN$ in water and the fractions (approx. 100 ml) were analyzed by TLC. The fractions containing the pure product (500 ml) were combined, concentrated under vacuum to remove $CH_3CN$, freeze-dried, and finally evaporated from 150 ml of absolute ethanol, to give 442 mg of a white, highly hygroscopic solid. Yield: 16%.

1H-NMR (DMSO-d6): δ (ppm) 1.38 (s, 9H) 1.58-1.75 (m, 4H), 3.03 (s, 9H), 3.29 (m, 2H), 3.45 (m, 1H), 6.49 (d, d, 1H); ESI(+)MS: m/z 275.2 [M+H]+.

Intermediate (11')(4-(S)-tert-Butoxycarbonylamino-5-(4-{4-[2,4-dichloro-3-(2,4-dimethyl-quinolin-8-yloxymethyl)benzenesulfonylamino]tetrahydro-pyran-4-carbonyl}piperazin-1-yl)-5-oxo-pentyl]trimethyl-ammonium chloride Intermediate (10'), 1.2 mmols, was dissolved in DMF and the solution was added with dicyclohexylcarbodiimide (1.2 eq) and HOBt (1.2 eq). The mixture was kept under stirring for 30 min, then added with diisopropylaminomethyl-polystyrene (1.5 eq) and intermediate (1') (1 eq). The mixture was left under stirring for 24 hours. The resin was filtered, the solvent was evaporated off and the residue was dissolved in water and ethyl acetate. The aqueous phase was separated and freeze-dried. The crude product was purified by preparative HPLC (column Vydac 218TP, C18, 250×50 mm, flow 60 ml/min, gradient 10% to 70% $CH_3CN/0.1\%$ TFA in 120 min, detector UV at 240 nm, collection 55 to 75 min) thereby affording intermediate (11') which was freeze-dried as a white solid. Yield: 46%. HPLC purity: 98% (20% B, 3%/min; Rt=7.68).

1H NMR (DMSO-d6) δ: 1.4 (s, 9H), 1.8-1.45 (m, 6H), 1.95-1.85 (m, 2H), 2.81 (m, 6H), 3.08 (s, 9H), 3.70-3.18 (m, 7H), 4.01-3.56 (5H, m), 4.57-4,45 (m, 1H), 5.59 (s, 2H), 7.25 (d, 1H), 7.90-7.43 (m, 4H), 8.02 (d, 1H), 8.85 (s, 1H). ESI(+)MS: m/z 863.2 [M+H]+.

(4-(S)-Amino-5-(4-{4-[2,4-dichloro-3-(2,4-dimethyl-quinolin-8-yloxymethyl)-benzenesulfonylamino]tetrahydropyran-4-carbonyl}piperazin-1-yl)-5-oxo-pentyl]trimethyl-ammonium chloride, dihydrochloride 0.45 mmols of (11') were added with 10 ml of HCl/dioxane 4M. The mixture was kept under stirring for 6 hours, the solvent was evaporated off and the residue was freeze-dried, thereby obtaining the final compound as a white solid. Yield: 87%. HPLC purity: 98% (20% B, 3%/min; Rt=5.14).

1H NMR (DMSO-d6) δ: 1.95-1.60 (m, 8H), 2.81 (m, 6H), 3.08 (s, 9H), 3.70-3.18 (m, 12H), 4.57-4,45 (m, 1H), 5.59 (s, 2H), 7.90-7.60 (m, 4H), 8.02 (d, 1H), 8.5 (s, 3H), 8.85 (s, 1H). ESI(+)MS: m/z 763.1 [M+H]+.

EXAMPLE 2

(4-(S)-Amino-5-(4-(4-(2,4-dichloro-3-(2-methyl-quinolin-8-yloxymethyl)-benzenesulfonylamino)tetrahydropyran-4-carbonyl)-piperazin-1-yl-)5-oxo-pentyl)-trimethylammonium chloride, hydrochloride 1H NMR (DMSO-d6) δ: 8.90 (1H, s), 8.47-8.34 (4H, m), 8.02 (1H, d), 7.81 (1H, d), 7.73-7.37 (4H, m), 5.62 (2H, s), 4.57-4,45 (1H, m), 4.01-3.56 (5H, m), 3.43-3.18 (7H, m), 3.06 (9H, s), 2.78-2.61 (4H, m), 2.89 (1H, s), 1.97-1.60 (9H, m). HPLC: tR=9.26 min. MS: [M]+749.

EXAMPLE 3

[5-(4-{4-[2,4-Dichloro-3-(2,4-dimethyl-quinolin-8-yloxymethyl)-benzene-sulfonylamino]tetrahydropyran-4-carbonyl}piperazin-1-yl)-5-oxo-pentyl]-trimethyl-ammonium trifluoroacetate.

1H-NMR (DMSO-d6): δ (ppm) 1.53 (s, 2H, m); 1.69 (m, 4H); 1.90 (m, 2H); 2.45 (t, 2H); 2.78 (m, 6H); 3.04 (9H, s); 3.23-3.57 (7H, m); 5.68 (2H, s); 7.38-8.18 (5H, m); 8.04 (1H, d, J=8.42 Hz); 8.82 (1H, s). HPLC: tR=5.65 min. MS: [M]+ 748.

EXAMPLE 4

[4-(S)-Amino-5-(4-{1-[2,4-dichloro-3-(2,4-dimethyl-quinolin-8-yloxymethyl)-benzenesulfonylamino] cyclopentanecarbonyl}piperazin-1-yl)-5-oxo-pentyl]-trimethyl-ammonium chloride, dihydrochloride.

1H NMR (DMSO-d6) δ: 8.90 (1H, s), 8.48 (3H, s), 8.02 (1H, d), 7.95-7.63 (3H, m), 5.59 (2H, s), 4.57-4,45 (1H, m), 3.97-3.24 (10H, m), 3.08 (9H, s), 2.95-2.61 (5H, m), 1.97-1.72 (8H, m), 1.42 (4H, s); HPLC: tR=5.88 min. MS: [M]+ 747.2.

Biological Activity

The evaluation of the B2 receptor affinity of the compounds of the present invention was carried out with studies of binding to the human B2 receptor expressed in CHO cells, following the procedure described by Bellucci, et al., Br. J. Pharmacol. 140:500-506 (2003); the binding values are reported expressed as pKi.

Antagonistic activity (expressed as pA2) was evaluated as the inhibition of the bradykinin-induced production of inositols in CHO cells transfected with B2 human receptor, according to the procedure described in Bellucci, et al., Br. J. Pharmacol. 140:500-506 (2003).

The in vivo activity of the compounds of the present invention was evaluated as effectiveness in inhibiting BK-induced bronchospasm in the guinea pig (Tramontana, et al., J. Pharmacol. Exp. Therap. 296:1051-1057 (2001)), measuring the it dose (it=intratracheal administration) (in nmols/kg) which inhibited by 80% bronchial constriction for at least 210 min.

The preferred compounds of the present invention were compared with those more structurally similar disclosed in WO03103671. It has surprisingly been found that the compounds of the invention have in vivo and in vitro activities higher than the structurally related analogues of WO03103671. Both the antagonistic activity test on cells transfected with the human receptor and the in vivo test are highly predictive of the expected dose for therapeutical applications in humans.

Abbreviations it=intratracheal administration; iv=intravenous administration; eq=equivalent; DCM=dichloromethane; MeOH=methanol; THF=tetrahydrofuran; DMSO=dimethylsulfoxide; DMF=dimethylformamide; AcOEt=ethyl acetate; AcOH=acetic acid; TFA=trifluoroacetic acid; NBS=Nα-bromosuccinimide; bpo=benzoyl peroxide; Boc=tert-butoxycarbonyl; HOBt=1-hydroxy-benzotriazole; EDC=1-ethyl-3-(3'-dimethylpropyl) carbodiimmide; DIPEA=diisopropylethylamine; HPLC=high pressure liquid chromatography; TLC=thin-layer chromatography; NMR=nuclear magnetic resonance; ESI=electron spray ionization; MS=mass spectrometry; FCC=Flash Column Chromatography; Rt=retention time.

The invention claimed is:

1. A pharmaceutically acceptable salt of the composition of matter of general formula (I)

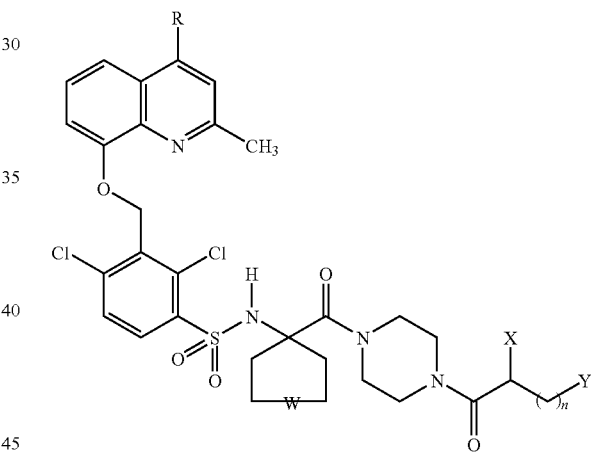

(I)

| Example | W | R | X | Y | n | pKi | pA2 | it Dose |
|---|---|---|---|---|---|---|---|---|
| WO03103671 ex 55 | bond | H | $NH_2$ | $NHC(=NH)NH_2$ | 3 | 8.7 | 8.4 | 300 |
| WO03103671 ex 63 | bond | $CH_3$ | $NH_2$ | $NH_2$ | 4 | 9.1 | 8.9 | 300 |
| WO03103671 ex 57 | bond | H | $NH_2$ | $N(CH_3)_2$ | 4 | 8.8 | 8.3 | 300 |
| WO03103671 ex 59 | bond | $CH_3$ | $NH_2$ | $N(CH_3)_2$ | 4 | 8.8 | 9.0 | 300 |
| WO03103671 ex 44 | bond | $CH_3$ | $NH_2$ | $NHC(=NEt)NHEt$ | 3 | 10.1 | 9.0 | 300 |
| WO03103671 ex 88 | bond | $CH_3$ | $N(CH_3)_3$ | $N(CH_3)_3$ | 4 | 9.7 | 8.2 | — |
| Example 1 | O | $CH_3$ | $NH_2$ | $N(CH_3)_3$ | 3 | 10.3 | 10.3 | 30 |
| Example 2 | O | H | $NH_2$ | $N(CH_3)_3$ | 3 | 10.2 | 9.7 | 100 |
| Example 3 | O | $CH_3$ | H | $N(CH_3)_3$ | 3 | 10.1 | 9.5 | 100 |
| Example 4 | bond | $CH_3$ | $NH_2$ | $N(CH_3)_3$ | 3 | 10.1 | 9.4 | 100 | in which

R is hydrogen or methyl;

W is an oxygen atom;

n=3;

X is hydrogen or a —$NR_1R_2$ amino group in which $R_1$ and $R_2$ can be independently hydrogen or selected from the group consisting of methyl, ethyl, n-propyl, or isopropyl;

Y is a —$NR_3R_4R_5$ quaternary ammonium group in which $R_3$, $R_4$, $R_5$ can be independently selected from the group consisting of methyl, ethyl, n-propyl, isopropyl, n-butyl, isobutyl, or n-pentyl; and the enantiomers and enantiomeric mixtures thereof.

2. The pharmaceutically acceptable salt of claim 1, which is a salt of an inorganic or organic acid selected from the group consisting of hydrochloric, hydrobromic, hydroiodic, sulfuric, phosphoric, acetic, trifluoroacetic, propionic, oxalic, malic, maleic, succinic, malonic, aspartic, or glutamic acid.

3. The pharmaceutically acceptable salt of claim 1, in which:

R is selected from hydrogen or methyl;

W is an oxygen atom;

n=3;

X is selected from hydrogen or a $NH_2$ group; and

Y is a —$N(CH_3)_3^+$ quaternary ammonium group.

4. The pharmaceutically acceptable salt of claim 3, which is (4-(S)-amino-5-(4-{4-[2,4-dichloro-3-(2,4-dimethyl-quinolin8yloxy-methyl) benzenesulfonylamino] tetrahydropyran-4carbonyl}-piperazin-1-yl)-5-oxo-pentyl] trimethyl-ammonium chloride, dihydrochloride.

5. The pharmaceutically acceptable salt of claim 3, which is (4-(S)-amino-5-(4-(4-(2,4-dichloro-3-(2-methyl-quinolin-8-yloxy-methyl)-benzenesulfonylamino)-tetrahydropyran-4-carbonyl)-piperazin-1-yl-)5-oxo-pentyl)-trimethyl-ammonium chloride, hydrochloride.

6. The pharmaceutically acceptable salt of claim 3, which is [5-(4-{4-[2,4-dichloro-3-(2,4-dimethyl-quinolin-8-yloxymethyl)-benzenesulfonylamino]tetrahydropyran-4-carbonyl}piperazin-1-yl)-5-oxo-pentyl]trimethyl-ammonium trifluoroacetate.

7. The pharmaceutically acceptable salt of claim 1, which is in the form of a racemic mixture.

8. The pharmaceutically acceptable salt of claim 1, which is in the form of an enantiomer.

9. A pharmaceutical composition comprising the pharmaceutically acceptable salt of claim 1, and a pharmaceutically acceptable excipient or carrier.

10. The pharmaceutical composition of claim 9, which is in a form selected from the group consisting of a tablet, capsule, granule, powder, solution, suspension or syrup.

11. The pharmaceutical composition of claim 9, wherein the excipient or carrier is selected from the group consisting of ligands, disintegrants, lubricants, fillers, stabilizing agents, diluents, dyes, flavors and wetting agents.

12. A method of treating a human patient having asthma or chronic bronchitis, comprising administration to the human patient of an effective dose of the composition of matter of claim 1.

13. The method of claim 12 wherein the administration comprises oral administration.

* * * * *

UNITED STATES PATENT AND TRADEMARK OFFICE
CERTIFICATE OF CORRECTION

| | | |
|---|---|---|
| PATENT NO. | : 7,645,759 B2 | Page 1 of 1 |
| APPLICATION NO. | : 11/786041 | |
| DATED | : January 12, 2010 | |
| INVENTOR(S) | : Patrizia Felicetti et al. | |

It is certified that error appears in the above-identified patent and that said Letters Patent is hereby corrected as shown below:

Column 15, line 25, "$NH_2$" should read -- —$NH_2$--.
Column 15, line 29, "quinolin8yloxy-methyl)" should read --quinolin-8-yloxy-methyl--.
Column 15, line 30, "pyran-4carbonyl" should read --pryan-4-carbonyl--.

Signed and Sealed this
Eighth Day of February, 2011

David J. Kappos
*Director of the United States Patent and Trademark Office*